United States Patent [19]

Le Van Mao

[11] Patent Number: 4,873,392
[45] Date of Patent: Oct. 10, 1989

[54] CATALYTIC CONVERSION OF AQUEOUS ETHANOL TO ETHYLENE

[75] Inventor: Raymond Le Van Mao, St-Laurent, Canada

[73] Assignee: Concordia University, Montreal, Canada

[21] Appl. No.: 185,911

[22] Filed: Apr. 25, 1988

[51] Int. Cl.$^4$ .............................................. C07C 6/00
[52] U.S. Cl. ................................................... 585/640
[58] Field of Search ........................................ 585/640

[56] References Cited

U.S. PATENT DOCUMENTS 4,052,479  10/1977  Chang et al. .......................... 585/640
4,670,620  6/1987  Jacobs et al. .......................... 585/640

Primary Examiner—Curtis R. Davis
Attorney, Agent, or Firm—Cushman, Darby & Cushman

[57] ABSTRACT

There is provided a process for converting diluted ethanol to ethylene which comprises heating an ethanol-containing fermentation broth thereby to vaporize a mixture of ethanol and water and contacting said vaporized mixture with a ZSM-5 zeolite catalyst selected from the group consisting of a ZSM-5 zeolite having a Si/Al atomic ratio of from 5 to 75 which has been treated with steam at a temperature ranging from 400° to 800° C. for a period of from 1 to 48 hours;

a ZSM-5 zeolite having a Si/Al atomic ratio of from 5 to 50 and wherein La or Ce ions have been incorporated in a weight percentage of 0.1 to 1.0% by ion exchange or in a weight percentage ranging from 0.1 to 5% by impregnation, and a ZSM-5 zeolite having a Si/Al of from 5 to 50 and impregnated with a 0.5 to 7% wt % of triflic acid, and recovering the ethylene thus produced.

3 Claims, No Drawings

CATALYTIC CONVERSION OF AQUEOUS ETHANOL TO ETHYLENE

FIELD OF THE INVENTION

The present invention relates to a novel process for the selective conversion of very dilute ethanol derived from a fermentation broth to ethylene. More particularly, the present invention relates to a process for converting aqueous ethanol to ethylene over a ZSM-5 zeolite (acid form) which has been treated with steam, or onto which triflic acid (trifluoromethanesulfonic acid) has been incorporated, or onto which La or Ce ions have been incorporated. The two latter catalysts give very high ethylene yield at lower reaction temperature.

This invention also includes the use of a vaporizer which allows the conversion of unpurified ethanol fermentation broth.

BACKGROUND OF THE INVENTION

The silica-rich ZSM-5 zeolite and its homologue, the ZSM-11 zeolite, belong to the crystalline alumno-silicate pentasil family. These zeolites are use in many catalytic reactions of industrial interest such as xylene isomerization, toluene disproportionation, benzene and toluene ethylation, and methanol-to-gasoline conversion among others. Their peculiar catalytic properties are mainly due to their regular framework with a pore size which is intermediate to the large pore sized zeolites (for instance, zeolites X and Y) and the small pore sized zeolites (for instance the A zeolites). The shape selectivity of the pentasil zeolites is the catalytic expression of many factors such as:

(a) the sieving effect, i.e. the capability of the zeolite to admit into its pores or to reject reactive molecules having a critical diameter falling within a well defined range;

(b) the (reverse) sieving effect, i.e. the capability of the zeolite to allow product molecules having a certain critical diameter to diffuse out of its pores. Thus, in the case of a product molecule having a diameter exceeding the pore size of the zeolite, this molecule will have to undergo additional cracking into a smaller molecule before diffusing out of the zeolite;

(c) the effect on the reaction intermediates, i.e. the capability of certain active sites to determine the length and geometry of reaction intermediate species.

In the dehydration-cracking of methanol, this third factor is enhanced by using a ZSM-5 zeolite in acid or H-form i.e. one in which nearly all the sodium ions originally present in the zeolite as synthesized, have been exchanged for protons. Thus, according to the scientific literature, the (H-form) ZSM-5 zeolites, when reacted with light alcohols, including particularly methanol and ethanol, give very similar product distributions. These results are in perfect agreement with theoretical studies on the reaction mechanism, which have identified an identical first reaction step leading to olefinic precursors, namely propylene and ethylene.

The acid sites in ZSM-5 zeolites are mainly located at the zeolite channel intersections and are also responsible for the formation of aromatics in the final products of methanol conversion. Although the "narrowness" of the zeolite channels restricts, as mentioned before, the size of reaction products to those having no more than 11 C-atoms, the acidity of the reactive sites promotes the formation of hydrocarbons having at least 4 carbon atoms from light olefinic precursors such as ethylene and propylene. Therefore, a modification of the acid sites of the ZSM-5 zeolites is warranted if the production of shorter hydrocarbons such as ethylene is desired.

In any event, it is now also thought that the acid character of the acid form of the ZSM-5 zeolites originates in the Bronsted centres created by the tetrahedral aluminum sites. By activating the zeolite at high temperature, Lewis acid sites are also formed by dehydroxylation of the zeolite surface.

According to the actual prior art, ethanol conversion over gamma-alumina mostly leads to the corresponding ether and only a small amount of ethylene is normally formed. Higher selectivities to ethylene may be obtained with very acidic aluminas and under certain reaction conditions.

Ethanol reacts over certain oxides such as thorium, chromium or titanium oxides to produce simultaneously ethylene and acetaldehyde, a dehydrogenation product. The decomposition of ethanol over supported thoria catalysts produces almost exclusively ethylene. However, conversion rates are low and an ethanol concentration of at least 90% is necessary to provide a significant yield in ethylene. In fact, if the dehydration of alcohol is performed over the afore mentioned thorium, chromium or titanium oxide catalysts with ethanol in very dilute aqueous solutions (2 to 19 vol % of ethanol in water), the yield in ethylene is low although the selectivity to ethylene in the product hydrocarbons can be very high. This is due to the fierce competition in the adsorption onto the catalyst surface, between the molecules of ethanol and water. The detrimental effect of water on the yield in ethylene is due to the stronger adsorption of water on the hydrophilic active sites of the catalyst.

The silica-rich ZSM-5 zeolites, on the other hand, exhibit a large hydrophobic surface which prevents saturation of the catalyst surface by water molecules.

In 1984, a study done by G. A. Aldridge el al. and published in Ind. Eng. Chem. Process Res. Dev. 23, 733–737 (1984) showed that the catalytic conversion of ethanol from fermentation broths to gasoline over a pentasil type zeolite was at the time the most efficient in terms of energy requirement. Such a process comprises two steps:

(a) distillation of the fermentation broth in order to obtain a 60 wt % ethanol aqueous solution (as optimum concentration of ethanol, suitable for the next catalytic step) and then;

(b) catalytic reaction at 300° C. after a compression of the resulting vapors up to 8 atm.

Of course, the major inconvenient of such a technique is the need to perform distillation of dilute ethanol solutions in order to obtain significant yields in the conversion of ethanol to gasoline.

This problem has been overcome in U.S. Pat. No. 4,698,452 which discloses a process for producing light olefins and ethylene in very high yields. This process comprises flowing an aqueous ethanol solution having an ethanol concentration ranging from 2 to 19% by volume through a modified pentasil-type zeolite catalyst at a temperature ranging from 300° to 450° C. The modified catalyst used in U.S. Pat. No. 4,698,452 is a pentasil-type zeolite in which Zn and Mn have been incorporated.

However, the process described in U.S. Pat. No. 4,698,452 is still quite expensive commercially because even though the distillation step has been eliminated, the conversion reaction still has to be performed at a temperature of at least 300° C.

The reaction temperature problem has been partially overcome in U.S. application Ser. No. 102474 filed Sept. 29, 1987, and now abandoned in the names of R. Le Van Mao and L. H. Dao. This application discloses the use of a steam-treated ZSM-5 zeolite in the production of ethylene from ethanol in water at very low concentrations.

U.S. application Ser. No. 179,547 filed Apr. 8, 1988 discloses the use of a ZSM-5 zeolite (acid form) onto which triflic acid (trifluoromethanesulfonic acid) has been incorporated.

Accordingly, it would appear highly desirable if a process could be provided for the conversion of ethanol derived from fermentation broth to ethylene without the necessity of purifying and/or distilling the fermentation broth and the necessity of catalytically converting the ethanol at high temperatures.

SUMMARY OF THE INVENTION

In accordance with the present invention, a fermentation broth is heated to a temperature sufficient to provide a vaporized mixture of ethanol and water and converting said ethanol by contact with a ZSM-5 zeolite catalyst selected from a ZSM-5 zeolite having a Si/Al atomic ratio of from 5 to 75 and which has been treated with steam at a temperature ranging from 400° to 800° C. for a period of from 1 to 48 hours, a ZSM-5 zeolite having a Si/Al atomic radio of from 5 to 50 and wherein La or Ce ions have been incorporated in a weight percentage of 0.1 to 1.0% by ion exchange or in a weight percentage ranging from 0.1 to 5% by impregnation and a ZSM-5 zeolite having a Si/Al ratio of from 5 to 50 and impregnated with 0.5 to 7 wt % of triflic acid.

Also in accordance with the present invention, an alcohol containing fermentation broth containing glucose, fermentation residues such as yeast and yeast nutrients, is evaporated at a temperature between the range of from 100° C. to 150° C. whereby ethanol and water are mainly evaporated while the glucose, and other non-volatile substances are retained in the fermentation broth. The concentration of the aqueous ethanol solution is from 2 to 15 weight %. The vaporized ethanol-water solution is then passed over the ZSM-5 zeolite catalyst which is not deactivated because of the absence of glucose.

The reaction parameters depend on the type of catalyst used and concern mainly the temperature and the weight hourly space velocity (W.H.S.V.). To achieve a high ethylene yield, the reaction temperature and the W.H.S.V. are set according to the Si/Al atomic ratio of the ZSM-5 zeolite used to prepare the final catalyst.

In all the cases, under the same reaction conditions, the lower the Si/Al atomic ratio of the ZSM-5 zeolite, the higher the ethylene yields. However, with a ZSM-5 zeolite having a Si/Al ratio lower than 10, the catalyst undergoes a rapid catalytic decay when the reaction is performed at a temperature higher than 275° C. Moreover, the higher the W.H.S.V., the lower the ethylene yields.

In the case of the steamed ZSM-5 zeolite (acid form) as previously described, the reaction temperature ranges from 250° C. to 450° C. and the W.H.S.V., from 0.1 $h^{-1}$ to 50 $h^{-1}$. The lowest temperature to achieve an ethylene yields of at least 95 wt % from an aqueous ethanol (10 wt %) when the reaction is carried out at a 3.2 $h^{-1}$ as W.H.S.V. and over a steamed ZSM-5 zeolite having a Si/Al atomic ratio of 20, is 275° C.

In the case of the ZSM-5 zeolite (acid form) into which La and Ce ions have been incorporated as previously described, the reaction temperatures ranges from 210° C. to 350° C. and the W.H.S.V., from 0.1 $h^{-1}$ to 50 h˙1. The lowest temperature to achieve an ethylene yields of at least 95 wt % from an aqueous ethanol (10 wt %) when the reaction is carried out at a 1.0 $h^{-1}$ as W.H.S.V. and over a so-modified ZSM-5 zeolite having a Si/Al atomic radio of 10, is 225° C.

In the case of the ZSM-5 zeolite (acid form) into which triflic acid has been incorporated as previously described, the reaction temperature ranges from 170° C. to 225° C. and the W.H.S.V., from 0.1 $h^{-1}$ to 50 $h^{-1}$. The lowest temperature to achieve an ethylene yields of at least 95 wt % from an aqueous ethanol (10 wt %) when the reaction is carried out at a 1.0 $h^{-1}$ as W.H.S.V. and over a so-modified ZSM-5 zeolite having a Si/Al atomic ratio of 10, is 190° C.

DETAILED DESCRIPTION AND PREFERRED EMBODIMENTS

The present invention relates to a process to convert a dilute aqueous solution of ethanol whose concentration ranges from 2 wt % to 15 wt % to ethylene using a modified silica rich zeolite. The zeolites which are directly concerned by the present invention belong to the family called ZSM pentasil family namely ZSM-5 and ZSM-11 type zeolites.

The ZSM-5 zeolite modification includes steaming the zeolite at high temperature, incorporating the La and Ce ions into the zeolite structure, and incorporating the triflic acid onto and binding it on the zeolite surface.
Steaming treatment of the ZSM-5 zeolite The ZSM-5 zeolite (acid form) having a Si/Al atomic ratio ranging from 5 to 75, is treated with steam at a temperature ranging from 400° C. to 800° C. for a period of time ranging from 1 hour to 48 hours. Incorporating the La and Ce ions into the zeolite structure La and Ce ions are incorporated by ion-exchange to a weight percentage ranging from 0.1 to 1.0% or by impregnation to a weight percentage ranging from 0.1 to 5% into a ZSM-5 zeolite (acid form) having a Si/Al atomic ratio ranging from 5 to 50. Incorporating the triflic acid onto and binding it to the zeolite surface Triflic acid (trifluoromethanesulfonic acid) is impregnated using acetone as solvent at a weight percentage of from 0.5 to 7% onto a ZSM-5 zeolite (acid form), and then allowed to react with the zeolite surface at a temperature ranging from 80° C. to 150° C. for a period of time ranging from 1 hour to 24 hours. The final catalyst may be activated in an inert medium at a temperature ranging from 180° C. to 275° C. for 1 to 12 hours.

CATALYTIC CONVERSION OF ETHANOL TO ETHYLENE

Conversion of ethanol in an aqueous solution having a concentration ranging from 2 to 15 weight % is usually effected by injecting the aqueous ethanol solution into a vaporizer-gas mixer. To simulate the real situation wherein the feed (the unpurified ethanol fermentation broth) contains also some leftover glucose, yeast and yeast fragments, yeast nutrients, as well as impurities coming from the previous steps (delignification, acid or enzymatic hydrolysis), glucose (and eventually some yeast) is added to the aqueous ethanol (concentration of glucose ranging from 0.3 to 5 wt %). Since glucose decomposes at 162° C. and if glucose and other impurities were sent along with the aqueous ethanol directly over the zeolite catalyst at high temperature, there would be a very rapid catalytic activity decay due to the poisoning effect of these compounds and the carbonaceous deposit (resulting from their decomposition) onto the active catalyst surface.

In order to overcome these problems, the vaporizer-gas mixer which is entirely heated at a temperature ranging from 110° C. to 150° C., is designed in such a way that it allows the vaporization of ethanol and also water and other volatile compounds. This device is capable to retain glucose, yeast, yeast nutrients and other non-volatile substances.

It basically consists of a cylindrical-body flask whose bottom is enlarged, and contains some glass or ceramics beads (to favor the evaporation) and eventually a non-volatile liquid medium (mineral oil, for instance). A drain is set at the flask bottom, in order to remove the non-volatile substances after a run, eventually by dissolving them in some water. The upper part of the flask is connected to the reactor and may have a (glass or ceramic) filter. Two inlets are made at circa the half level of the flask: one to let the pumping in of the aqueous ethanol solution and the other one (optional), to flow in the stripping (or carrier) inert gas such as nitrogen (the flow rate may range from 2 to 30 ml/mn).

All the non volatile substances (including glucose, and yeast and yeast nutrients) are retained at the bottom and volatile substances (ethanol, steam, etc) are flown through a catalyst bed containing the catalyst in bead form having a density that can range between 0.5 and 1.5 g/cm$^3$.

The temperature of the catalyst bed which is set in a tubular reactor contained inside a furnace may range between 170° and 450° C. according to the type of catalyst used, as afore mentioned. The gaseous mixture flowing out of the reactor is then run through a series of condensers maintained at a temperature ranging between 5° and 10° C. to a liquid collector immersed in an ice bath followed by a cylinder from which gas sampling may be carried out. The resulting liquid and gaseous products are analysed through gas or chromatography.

In the following examples, yield of product hydrocarbon is defined as the yield in product hydrocarbon recovered during the run divided by the maximum theoretical yield in hydrocarbons according to the equation:

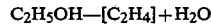

$$C_2H_5OH \rightarrow [C_2H_4] + H_2O$$

The following examples are given to illustrate rather than limit the scope of the present invention.

EXAMPLE 1

Preparation of the steamed ZSM-5 zeolite (acid form), the H-ZSM-5 (21,St) sample.

110 g of Baker silica gel dried at 120° C. for 12 hours, and having a silica content of 90 wt % were mixed with an aqueous solution containing 110 g of tetrapropylammonium bromide (Aldrich) and 7 g of NaOH dissolved in 300 m of distilled water. The suspension was heated at 80° C. under vigorous stirring for one hour. Then a solution prepared from 11 g of sodium aluminate containing 46.79 wt % of alumina and 28.44 wt % of sodium oxide dissolved in 90 ml of distilled water was added. Heating was continued at 80° C. with vigorous stirring for 10 minutes. The suspension was then transferred into a Parr autoclave lined with Teflon®, and heated for 10 days at 170° C. ±5° C. After cooling, the suspension was discharged from the autoclave and filtered, the solid was washed with distilled water until the washing liquid had a pH lower than 9 and was dried at 120° C. for 12 hours and activated in the air at 550° C. for 12 hours.

The resulting solid was brought in contact with an aqueous solution of ammonium chloride (5 wt %), using 10 ml of solution per gram of compound. The suspension was heated at 80° C. under reflux with moderate stirring. After 1 hour of heating, the suspension was allowed to settle and the liquid was then rapidly removed. A fresh volume of ammonium chloride solution was added and the suspension was again heated for another hour. The same procedure was repeated for several times so that the entire operation lasted 5 hours. The suspension was filtered and the solid was washed until Cl$^-$ ions were no longer present in the washing solution. The compound was dried at 120° C. for 12 hours and then activated in the air for 12 hours at 550° C. The resulting acid form of the H-ZSM-5 (21,St) had the following chemical composition (% by weight): silica=95.4; alumina=4.5 and Na$_2$O=0.1 (Si/Al atomic ratio=21). Its degree of crystallinity was 100%, when determined according to the method of Le Van Mao et al. (Canadian Journal of Chemistry 63, 3464 (1985)).

The final catalyst form was prepared according to the following procedure: the previously obtained solid was intimately mixed with bentonite (20 wt %) and made into a paste with distilled water, 1 ml of water was used for each gram of the solid. Then, the extrudates were dried at 120° C. for 12 hours and activated in the air at 550° C. for 12 hours.

Prior to the catalyst testing in the Bioethanol-to-Ethylene reaction, the catalyst was treated with steam at 500° C. for 4 hours.

Catalytic testing of the H-ZSM-5 (21,St) sample.

The resulting H-ZSM-5 (21,ST) was then tested in the B.E.T.E. reaction in the presence of a feed which contains 10 wt % of ethanol and 2 wt % glucose dissolved in water. The following reaction parameters were used: T=275° C. and various W.H.S.V. Table 1 reports such catalytic data.

TABLE 1

| Catalytic data of the H-ZSM-5 (21,St) catalyst Reaction parameters = T = 275° C. Feed: 10 wt % ethanol and 2 wt % glucose in water. | | |
|---|---|---|
| W.H.S.V | Product yield (wt %) | |
| (h$^{-1}$) | Ethylene | Other hydrocarbons |
| 3.2 | 99.4 | 0.3 |
| 6.4 | 88.2 | 0.4 |
| 12.8 | 61.7 | 0.1 |
| 25.6 | 32.1 | 0.0 |
| 38.5 | 20.1 | 0.0 |

It is interesting to mention that with such a vaporizer, there was no significant decrease in the ethylene yield even after more than 100 hours of reaction (test performed with the W.H.S.V.=3.2 h$^{-1}$) whereas a direct injection of the feed to the preheating zone led to a bothersome carbon deposit in the preheating zone and a noticeable catalytic activity decay after 20 hours of reaction.

EXAMPLE 2

Preparation of the ZSM-5 zeolite (acid form), the H-ZSM-5 (10,powder).

The same preparation procedure as previously described was used except for the initial gel composition used for the zeolite synthesis which comprises 110 g of silica gel Baker and 22 g of sodium aluminate Fischer. The resulting acid-form of the ZSM-5 zeolite, called H-ZSM-5 (10,powder), had the following chemical composition (by weight): silica=90.8; alumina=9.1 and $Na_2O$=0.1 (Si/Al atomic ratio=10). Its degree of crystallinity was 94%.

Incorporation of La and Ce ions.

The incorporation of La (or Ce) ions into the H-ZSM-5 (10,powder) was done according to the following procedure. The H-ZSM-5 (10,powder) was brought in contact with an aqueous solution (2 wt %) of lanthanium (lll) nitrate hexahydrate or cerium (lll) nitrate hexahydrate, both from Aldrich (99%), using 10 ml of solution per gram of zeolite. The suspension was moderately stirred (room temperature) for 1 hour, then filtered and the solid was washed with distilled water. The compound was dried at 120° C. for 12 hours and then activated in the air for 12 hours at 550° C.

The resulting La-H-ZSM-5 (10) solid has a lanthanium content of 0.7 wt % while the Ce-H-ZSM-5 (10) has a cerium content of 0.6 wt %.

The final catalysts were obtained by extrusion in the presence of bentonite as binder (see Example 1). Catalytic testing of the La-H-ZSM-5 (10) and Ce-H-ZSM-5 (10).

The resulting catalysts were then tested in the B.E.T.E. reaction in the presence of aqueous ethanol (10 wt %) which also contains glucose (2 wt %). Table 2 reports the catalytic data of the La-H-ZSM-5 (10) and the reference sample, the H-ZSM-5 (10). Ce-H-ZSM-5 (10) gave similar catalytic data as La-H-ZSM-5 (10). The reference catalyst was obtained by extrusion in the presence of bentonite as binder (see Example 1).

TABLE 2

Catalytic data of the La-H-ZSM-5 (10) and the reference catalyst, the H-ZSM-5 (10)
(Reaction parameters: W.H.S.V. = 1 $h^{-1}$ and feed = 10 wt % ethanol and 2 wt % glucose in water)

| Catalyst | Reaction temperature (°C.) | Product yield (wt %) Ethylene | Other hydrocarbons |
|---|---|---|---|
| La-H-ZSM-5 (10) | 225 | 94.9 | 3.5 |
| La-H-ZSM-5 (10) | 215 | 72.5 | 2.7 |
| H-ZSM-5 (10) | 225 | 26.2 | 0.1 |
| H-ZSM-5 (10) | 200 | 14.0 | 0.0 |

EXAMPLE 3

Preparation of the ZSM-5 zeolite (acid form) with triflic acid incorporated, the H-ZSM-5 (10)/TFA (2).

The incorporation of triflic acid onto the H-ZSM-5 (10,powder) was done according to the following procedure: 0.2 g of triflic acid (TFA or trifluoromethanesulfonic acid, $CF_3SO_3H$) 98% from Fluka Chemie AG were dissolved in 15 ml of pure acetone. This solution was then slowly added to 10g of H-ZSM-5 (10,powder) under moderate stirring. The resulting suspension was allowed to settle and dry in the air at room temperature. The obtained solid was then heated at 120° C. for 12 hours.

The final catalyst was prepared by extrusion in the presence of bentonite as binder (see Example 1).

Catalytic testing of the H-ZSM-5 (10)/TFA (2).

The resulting catalyst was tested in the B.E.T.E. reaction in the presence of aqueous ethanol (10 wt %) which also contains glucose (2 wt %). Table 3 reports the catalytic data of the H-ZSM-5 (10 / TFA (2).

TABLE 3

Catalytic data of the H-ZSM-5 (10)/TFA (2)
(Reactions parameters: W.H.S.V. = 1 $h^{-1}$ and feed = 10 wt % ethanol and 2 wt % glucose in water)

| Reaction temperature (°C.) | Product yield (wt %) Ethylene | Other hydrocarbons |
|---|---|---|
| 205 | 95.8 | 3.4 |
| 200 | 97.2 | 0.1 |
| 190 | 94.6 | 0.2 |
| 180 | 73.3 | 0.6 |

I claim:

1. A process for converting diluted ethanol to ethylene which comprises:
    (a) heating an ethanol-containing fermentation broth thereby to vaporize a mixture of ethanol and water,
    (b) contacting said vaporized mixture with a ZSM-5 zeolite catalyst having a Si/Al ratio from 5 to 50 and impregnated with 0.5 to 7 wt % of triflic acid, and
    (c) recovering the ethylene thus produced.
2. The process of claim 1, wherein the reaction between said vaporized mixture is carried out with the ZSM-5 having triflic acid incorporated therein at a temperature of from 170° to 225° C.
3. The process of claim 2, wherein the Si/Al atomic ratio of the zeolite is 10 and the reaction temperature is 190° C.